US00PP22344P2

(12) United States Plant Patent
Westhoff

(10) Patent No.: US PP22,344 P2
(45) Date of Patent: Dec. 13, 2011

(54) ***SCAEVOLA* PLANT NAMED 'WESSCAESUN'**

(50) Latin Name: *Scaevola aemula*
Varietal Denomination: Wesscaesun

(75) Inventor: Heinrich Westhoff, Südlohn (DE)

(73) Assignee: Gartenbau und Spezialkulturen Westhoff GbR, Südlohn (DE)

( * ) Notice: Subject to any disclaimer, the term of this patent is extended or adjusted under 35 U.S.C. 154(b) by 111 days.

(21) Appl. No.: 12/658,048

(22) Filed: Feb. 1, 2010

(51) Int. Cl.
*A01H 5/00* (2006.01)

(52) U.S. Cl. ..... Plt./363

(58) Field of Classification Search ..... Plt./363
See application file for complete search history.

(56) References Cited

U.S. PATENT DOCUMENTS

| | | | | |
|---|---|---|---|---|
| PP19,703 | P2 * | 2/2009 | Westhoff | Plt./363 |
| PP19,728 | P2 * | 2/2009 | Heinrich | Plt./363 |
| PP19,729 | P2 * | 2/2009 | Heinrich | Plt./363 |

OTHER PUBLICATIONS

UPOV ROM GTITM Computer Database, GTI Jouve Retrieval Software 2011/01 Citation for 'Wesscaesun'.*

* cited by examiner

*Primary Examiner* — Wendy C Haas
(74) *Attorney, Agent, or Firm* — C. A. Whealy

(57) ABSTRACT

A new and distinct cultivar of *Scaevola* plant named 'Wesscaesun', characterized by its trailing plant habit; freely branching habit; small to medium-sized leaves; freely flowering habit; and bright and light yellow-colored flowers.

1 Drawing Sheet

Botanical designation: *Scaevola aemula.*
Cultivar denomination: 'WESSCAESUN'.

BACKGROUND OF THE INVENTION

The present invention relates to a new and distinct cultivar of *Scaevola* plant, botanically known as *Scaevola aemula*, and hereinafter referred to by the name 'Wesscaesun'.

The new *Scaevola* plant is a product of a planned breeding program conducted by the Inventor in Südlohn, Germany. The objective of the breeding program is to create new compact and freely-branching *Scaevola* cultivars with attractive and unique flower coloration.

The new *Scaevola* plant originated from a cross-pollination made by the Inventor in Südlohn, Germany in 2007 of a proprietary selection of *Scaevola aemula* identified as code number 07P010, not patented, as the female, or seed, parent with a proprietary selection of *Scaevola aemula* identified as code number 03PSC00, not patented, as the male, or pollen, parent. The new *Scaevola* plant was discovered and selected by the Inventor as a flowering plant within the progeny of the stated cross-pollination in a controlled greenhouse environment in Südlohn, Germany in 2009.

Asexual reproduction of the new *Scaevola* plant by vegetative cuttings in a controlled environment in Südlohn, Germany since 2009, has shown that the unique features of this new *Scaevola* plant are stable and reproduced true to type in successive generations.

SUMMARY OF THE INVENTION

Plants of the new *Scaevola* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Wesscaesun'. These characteristics in combination distinguish 'Wesscaesun' as a new and distinct cultivar of *Scaevola:*

1. Trailing plant habit.
2. Freely branching habit.
3. Small to medium-sized leaves.
4. Freely flowering habit.
5. Bright and light yellow-colored flowers.

Plants of the new *Scaevola* can be compared to plants of the female parent selection. Plants of the new *Scaevola* differ from plants of the female parent selection in the following characteristics:

1. Plants of the new *Scaevola* have smaller and more serrated leaves than plants of the female parent selection.
2. Plants of the new *Scaevola* have smaller flowers than plants of the female parent selection.
3. Plants of the new *Scaevola* and the female parent selection differ in flower color as plants of the female parent selection have white-colored flowers.

Plants of the new *Scaevola* can be compared to plants of the male parent selection. Plants of the new *Scaevola* differ from plants of the male parent selection in the following characteristics:

1. Plants of the new *Scaevola* are more freely branching than plants of the male parent selection.
2. Plants of the new *Scaevola* have finer lateral branches than plants of the male parent selection.
3. Plants of the new *Scaevola* and the male parent selection differ in flower color as plants of the male parent selection have white-colored flowers.

Plants of the new *Scaevola* can be compared to plants of *Scaevola aemula* 'Wesscaetowhi', disclosed in U.S. Plant Pat. No. 19,728. In side-by-side comparisons conducted in Südlohn, Germany, plants of the new *Scaevola* differed from plants of 'Wesscaetowhi' in the following characteristics:

1. Plants of the new *Scaevola* were larger and more trailing than plants of 'Wesscaetowhi'.
2. Leaf margins of plants of the new *Scaevola* were more serrated than leaf margins of plants of 'Wesscaetowhi'.
3. Plants of the new *Scaevola* had smaller flowers than plants of 'Wesscaetowhi'.
4. Flowers of plants of the new *Scaevola* had slightly narrower petals than flowers of plants of 'Wesscaetowhi'.
5. Plants of the new *Scaevola* and 'Wesscaetowhi' differed in flower color as plants of 'Wesscaetowhi' had white-colored flowers.

Plants of the new *Scaevola* can also be compared to plants of *Scaevola aemula* 'Wesscaecryimp', disclosed in U.S. Plant Pat. No. 19,703. In side-by-side comparisons conducted in Südlohn, Germany, plants of the new *Scaevola* differed from plants of 'Wesscaecryimp' in the following characteristics:

1. Plants of the new *Scaevola* were not as freely branching as plants of 'Wesscaecryimp'.
2. Leaf margins of plants of the new *Scaevola* were more serrated than leaf margins of plants of 'Wesscaecryimp'.
3. Plants of the new *Scaevola* had smaller flowers than plants of 'Wesscaecryimp'.
4. Flowers of plants of the new *Scaevola* had smaller sepals than flowers of plants of 'Wesscaecryimp'.
5. Plants of the new *Scaevola* and 'Wesscaecryimp' differed in flower color as plants of 'Wesscaecryimp' had white-colored flowers.

BRIEF DESCRIPTION OF THE PHOTOGRAPHS

The accompanying colored photographs illustrate the overall appearance of the new *Scaevola* plant, showing the colors as true as it is reasonably possible to obtain in colored reproductions of this type. Colors in the photographs may differ slightly from the color values cited in the detailed botanical description which accurately describe the colors of the new *Scaevola* plant.

The photograph at the top of the sheet comprises a top perspective view of a typical flowering plant of 'Wesscaesun' grown in a container.

The photograph at the bottom of the sheet is a close-up view of typical flowers of 'Wesscaesun'.

DETAILED BOTANICAL DESCRIPTION

The aforementioned photographs and following observations, measurements and values describe plants grown during the summer in Südlohn, Germany in 12-cm containers in a glass-covered greenhouse under conditions which closely approximate commercial production. During the production of the plants, day temperatures ranged from 20° C. to 25° C., night temperatures ranged from about 16° C. to 18° C. and light levels ranging from 3,000 lux to 50,000 lux. Plants were 25 weeks old when the photographs and the description were taken. In the description, color references are made to The Royal Horticultural Society Colour Chart, 2001 Edition, except where general terms of ordinary dictionary significance are used.

Botanical classification: *Scaevola aemula* 'Wesscaesun'.

Parentage:

*Female, or seed, parent.*—Proprietary selection of *Scaevola aemula* identified as code number 07P010, not patented.

*Male or pollen parent.*—Proprietary selection of *Scaevola aemula* identified as code number 03PSC00, not patented.

Propagation:

*Type.*—By vegetative cuttings.

*Time to initiate roots, summer.*—About 21 to 25 days at 20° C.

*Time to initiate roots, winter.*—About 23 to 28 days at 20° C.

*Time to develop roots, summer.*—About 30 days at 20° C.

*Time to develop roots, winter.*—About 35 days at 20° C.

*Root description.*—Medium in thickness, fibrous; color, close to 158A.

*Rooting habit.*—Freely branching; moderately dense to dense.

Plant description:

*Plant form and growth habit.*—Trailing plant habit; roughly spherical in shape; vigorous growth habit.

*Branching habit.*—Freely branching, about four to eight lateral branches develop per plant.

*Plant height.*—About 15 cm to 17 cm.

*Plant diameter (area of spread).*—About 45 cm.

*Lateral branches.*—Length: About 15 cm to 28 cm. Diameter: About 2 mm. Internode length: About 2.4 cm. Texture: Slightly pubescent. Color: Close to 146A to 146B.

*Leaves.*—Arrangement: Alternate, simple; sessile. Length: About 4 cm to 6.1 cm. Width: About 2.1 cm. Shape: Spatulate to ovate. Apex: Acute. Base: Attenuate. Margin: Serrated. Texture, upper and lower surfaces: Densely pubescent; leathery. Venation pattern: Pinnate, arcuate. Color: Developing leaves, upper surface: Close to 147A. Developing leaves, lower surface: Close to 147B. Fully expanded leaves, upper surface: Close to 147A to 147B; venation, close to 147A to 147B. Fully expanded leaves, lower surface: Close to 147C; venation, close to 147C.

Flower description:

*Flower type and shape.*—Zygomorphic, semi-circular, fan-shaped flowers with five petals fused at the base to form a tubular flower throat; flowers sessile; flower throat open along the upper surface exposing the reproductive organs.

*Flower arrangement and aspect.*—Solitary flowers arise from leaf axils; flowers face mostly outwardly.

*Quantity of flowers.*—Freely flowering habit, typically about three to nine flowers per flower cluster.

*Fragrance.*—None detected.

*Flowering time.*—Plants flower continuously from spring to the autumn in Germany.

*Flower longevity.*—Flowers typically last about a week on the plant; flowers not persistent.

*Flower cluster height.*—About 7 cm to 13 cm.

*Flower cluster width.*—About 5 cm.

*Flower buds.*—Shape: Lanceolate. Length: About 5 mm to 15 mm. Diameter: About 2.3 mm. Color: Close to 144A to 144B.

*Flowers.*—Length: About 1.4 cm. Width: About 2.2 cm. Flower throat diameter, apex: About 2.5 mm to 3 mm. Flower tube length: About 1.2 cm. Flower tube diameter, base: About 1.5 mm to 2.5 mm.

*Petals.*—Quantity: Five, fused at base. Shape: Oblanceolate. Apex: Cuspidate. Margin: Entire. Length, above tube: About 1.3 cm. Width, above tube: About 5 mm. Texture, upper and lower surfaces: Smooth, glabrous. Color: When opening, upper surface: Close to 5A to 5C. When opening, lower surface: Close to 5C to 5D. Fully opened, upper surface: Close to 7A;

towards the margins, close to 8D. Fully opened, lower surface: Close to 8B to 8D. Throat: Between 144C and N144B. Tube: Between N144A and 151D.

*Sepals.*—Quantity and arrangement: One large and two smaller sepals in a single whorl fused at the base. Length, larger sepal: About 1.6 cm. Length, smaller sepals: About 9 mm. Width, larger sepal: About 2.5 mm. Width, smaller sepals: About 1 mm. Shape, larger sepal: Lanceolate. Shape, smaller sepals: Acicular. Apex, all sepals: Acute. Margin, larger sepal: Indented. Margin, smaller sepals: Entire. Texture, upper and lower surfaces, all sepals: Pubescent. Color, all sepals, upper surface: Close to 147A. Color, all sepals, lower surface: Close to 147B.

*Peduncles.*—Length: About 7 cm to 13 cm. Diameter: About 2 mm. Strength: Strong, flexible. Texture: Smooth, glabrous. Color: Close to 146B.

*Reproductive organs.*—Androecium: Stamen quantity per flower: About five. Filament length: About 3 mm. Filament color: Close to 145D. Anther shape: Ovate. Anther length: About 2 mm. Anther diameter: About 1 mm. Anther color: Close to 11B. Pollen: Moderate. Pollen color: Close to 11A.

*Gynoecium.*—Pistil quantity per flower: One. Pistil length: About 1.5 cm. Style length: About 1 cm to 1.2 cm. Style color: Close to 145A to 145B. Stigma shape: Elongate. Stigma color, immature: Close to 155D; center, close to 144A. Stigma color, mature: Close to 11B to 11C. Ovary color: Close to 144A.

*Seeds/fruits.*—Seed and fruit development have not been observed.

Temperature tolerance: Plants of the new *Scaevola* have been observed to tolerate temperatures from about 2° C. to about 30° C.

Pathogen/pest resistance: Plants of the new *Scaevola* have not been shown to be resistant to pathogens and pests common to *Scaevola.*

It is claimed:

1. A new and distinct *Scaevola* plant named 'Wesscaesun' as illustrated and described.

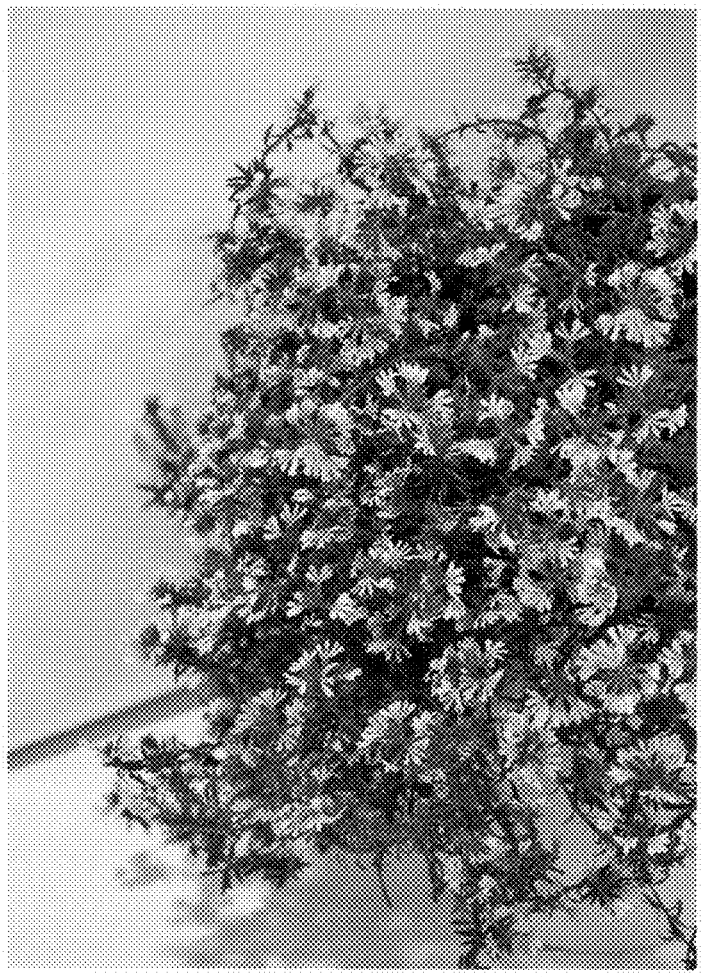
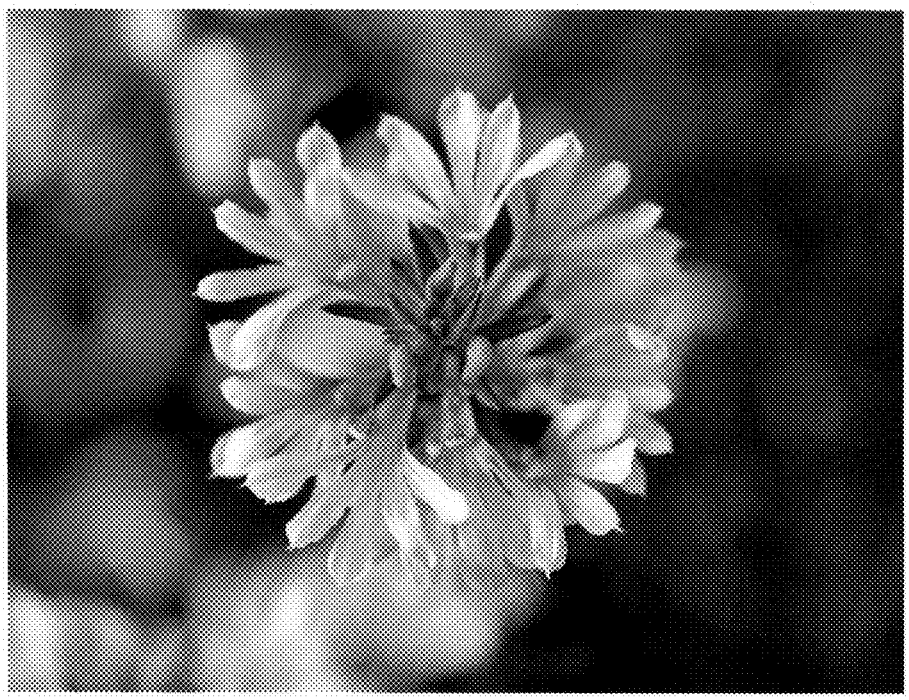

* * * * *